(12) United States Patent
Tanabe et al.

(10) Patent No.: US 6,589,937 B1
(45) Date of Patent: Jul. 8, 2003

(54) PEPTIDES AND NOOTROPIC AGENT

(75) Inventors: Shuichi Tanabe, Tokyo (JP); Yoshiyuki Shishido, Tokyo (JP); Masayoshi Furushiro, Tokyo (JP); Kunio Kado, Tokyo (JP); Shusuke Hashimoto, Tokyo (JP); Teruo Yokokura, Tokyo (JP); Tetsuya Terasaki, Chiba (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/171,245

(22) PCT Filed: Apr. 15, 1997

(86) PCT No.: PCT/JP97/01294

§ 371 (c)(1),
(2), (4) Date: Oct. 14, 1998

(87) PCT Pub. No.: WO97/39026

PCT Pub. Date: Oct. 23, 1997

(30) Foreign Application Priority Data

Apr. 15, 1996 (JP) ............................................... 8-115299

(51) Int. Cl.[7] .......................... A61K 38/03; C07K 7/06; C07K 7/08
(52) U.S. Cl. ............................. 514/14; 514/15; 514/17; 530/323; 530/329; 530/330; 530/331; 530/327; 530/328
(58) Field of Search .............................. 514/17, 14, 15; 530/323, 329, 330, 331, 327, 328

(56) References Cited

U.S. PATENT DOCUMENTS

| | | | |
|---|---|---|---|
| 4,487,765 A | * 12/1984 | de Wied | 424/177 |
| 4,748,154 A | 5/1988 | Goto et al. | 514/16 |
| 5,112,947 A | 5/1992 | Masaki et al. | 530/329 |
| 5,180,712 A | 1/1993 | Isowa et al. | 514/16 |
| 5,312,811 A | 5/1994 | Masaki et al. | 514/16 |
| 5,349,050 A | 9/1994 | Masaki et al. | 530/330 |

FOREIGN PATENT DOCUMENTS

| | | | |
|---|---|---|---|
| EP | 0 354 820 A | 2/1990 | |
| JP | A 54-73133 | 12/1978 | |
| JP | A 55-55120 | 2/1979 | |
| JP | A S59-93036 | 5/1984 | |
| JP | A S62-234095 | 10/1987 | |
| JP | H2-53734 | * 2/1990 | |
| JP | H2-53799 | * 2/1990 | |
| JP | A H2-53800 | 2/1990 | |
| JP | A H2-273694 | 11/1990 | |
| JP | A H2-273696 | 11/1990 | |
| JP | A H2-273699 | 11/1990 | |

OTHER PUBLICATIONS

Ader et al., *Psychon. Sci.*, 26:125–128, 1972.
de Wied et al., *Nature*, 308:276–278, 1984.
William M. Pardridge, *Peptide Drug Delivery to the Brain*, p. 189–218, 1991.
Hirokawa, *Development of Drugs*, 4:134–149, 1991.
Pardridge, *Pharmacology & Toxicology*, 71:3–10, 1992.
Kovacs et al., *Pharmacological Review*, 46:269–291, 1994.
Terasaki, *Journal of Controlled Release*, 29:163–169, 1994.
Terasaki et al., *Peptide–Based Drug Design*, p. 298–316, 1995.

* cited by examiner

Primary Examiner—Christopher S. F. Low
Assistant Examiner—Anish Gupta
(74) Attorney, Agent, or Firm—Wolf, Greenfield & Sacks, P.C.

(57) ABSTRACT

New peptides represented by the following general formula

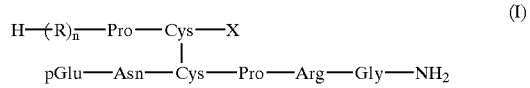

(I)

(wherein X is OH or $NH_2$, R is an amino acid residue selected from Arg, His, Lys, Methyl-Arg or Methyl-Tyr, n is an integer of 1–4, and in the case that n is 2–4, R may be identical with or different from each other) and an anti-dementia drug which contains one or more of these new peptides and has a high blood brain barrier (BBB) permeability and furthermore is low in a side effect.

20 Claims, 9 Drawing Sheets

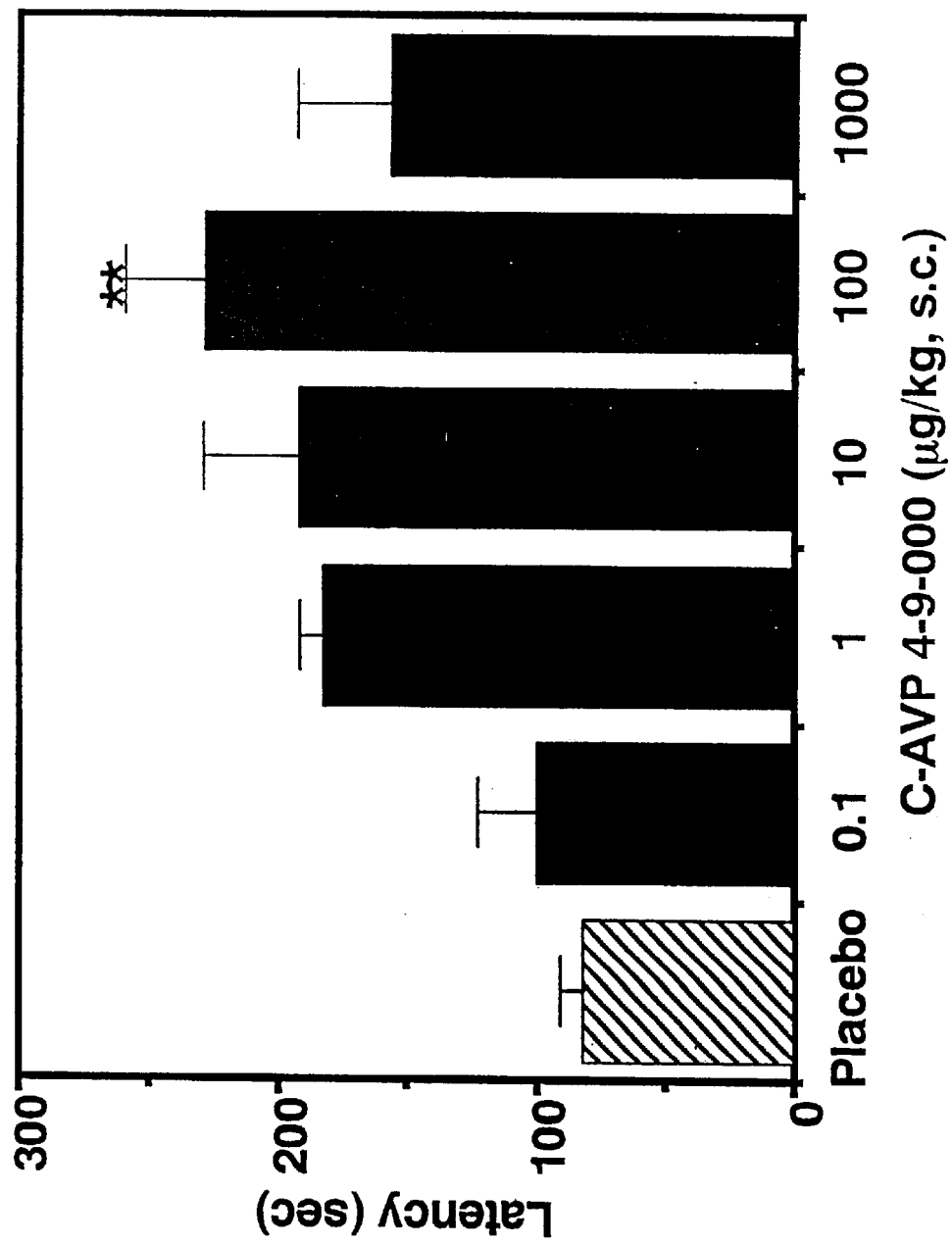
Fig. 2 – B

SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: DISULFID
<222> LOCATION: (6)...(6)
<223> OTHER INFORMATION: Disulfide bond between Cys in position 6 of SEQ
      ID NO: 1 and Cys in position 3 of SEQ ID NO:2.

```
<220> FEATURE:
<221> NAME/KEY: VARIANT
<222> LOCATION: (1)...(4)
<223> OTHER INFORMATION: Xaa is Arg, His, Lys, N-methyl-Arg or
      N-methyl-Tyr; 0-3 of the Xaa may be missing; the Xaa may be
      identical with or different from each other

<400> SEQUENCE: 1

Xaa Xaa Xaa Xaa Pro Cys
 1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)...(1)
<223> OTHER INFORMATION: Pyrrolidone Carboxylic Acid
<220> FEATURE:
<221> NAME/KEY: DISULFID
<222> LOCATION: (3)...(3)
<223> OTHER INFORMATION: Disulfide bond between Cys in position 3 of SEQ
      ID NO: 2 and Cys in position 6 of SEQ ID NO: 1.

<400> SEQUENCE: 2

Glu Asn Cys Pro Arg Gly
 1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Arg His Pro Cys
 1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)...(1)
<223> OTHER INFORMATION: Methylation
<220> FEATURE:
<221> NAME/KEY: MOD_RES
<222> LOCATION: (3)...(3)
<223> OTHER INFORMATION: Methylation

<400> SEQUENCE: 4

Tyr Arg Arg His
 1

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)...(1)
<223> OTHER INFORMATION: Methylation
```

<400> SEQUENCE: 5

Tyr Arg Arg His
1

PEPTIDES AND NOOTROPIC AGENT

FIELDS OF INDUSTRIAL APPLICATION

The invention relates to a new peptide having an improved effect of the brain function and an anti-dementia effect, and to an anti-dementia drug.

BACKGROUND ART

Anti-dementia drugs are classified into the first, second and third generations according to their action mechanisms and their chronological development ages. In the first generation are included the drugs already marketed such as calcium hopantenate (trade name: Hopate), indeloxazine hydrochloride (trade name: Elen) and idebenone (trade name: Avan), expressing the protection of the brain function and a metabolic acceleration action. In the second generation are included a prolyl endopeptidase (PEP) inhibitor and a choline esterase inhibitor which is marketing. Furthermore, in recent years the application of a biological substance is tried as the third generation anti-dementia drug, and neuropeptides with neuron growth factor (NGF) as the head of the list, argine vasopressin (AVP), thyroid hormone releasing hormone (TRH), vasoactive intestinal peptide (VIP), etc., are noticed.

Among these AVP is classified as the third generation anti-dementia drug as described above, though, the history of its research is long, and it has been studied as a peptide hormone having a strong anti-dementia activity since the report of D. Weid in 1984 (see Nature, 308, 276–278, 1984). Additionally, the number of its reports' publications exceeds 100 annually since 1980s, hereby indicating that it is a notable substance in the field of neurophsiology. Furthermore, the above PEP inhibitors are developed aiming to inhibit the intracerebral metabolism of AVP. From these, it can be estimated that the expectation for the anti-dementia activity of AVP is extremely high.

On one hand, problems in case of applying AVP as an anti-dementia drug are (1) the intrinsic activity of AVP, that is to say, elevation of blood pressure and diuretic action, (2) the instability in body due to the proline cleavage by PEP, and (3) a low blood-brain barrier (BBB) permeability. Owing to these, a number of AVP derivatives have been synthesized to improve these points and to further strengthen the anti-dementia activities. Such a research like this has been undertaken at a drug development level, and a lot of patent applications have been made (for example, JP, A, S54-73133, JP, A, S55-55120, JP, A, S62-234095, JP, A, H2-53797, JP, A, H2-53800, JP, A, H2-273696, JP, A, H2-273694, JP, A, H2-273699, etc.).

By up-to-date reports, as to the above (1)–(3) problems the following solutions are found for (1) and (2).

(1) The side effects on blood pressure and urine volume can be reduced by using AVP as the 4–9 fragment pGlu-Asn-Cys-Pro-Arg-Gly-NH$_2$ (AVP 4-9)(SEQ ID NO:2).

(2) By converting the amino acid proline of AVP 4-9 into D form, the metabolism by PEP can be avoided keeping the anti-dementia activity.

On one hand, as to the increase of a BBB permeability as mentioned in the above (3), it has currently been tried to increase the BBB permeability by increasing lipophilicity. However, in case of increasing a drug lipophilicity, not only the BBB permeability but the transition to all tissues increase, resulting to the decreasing phenomenon of area under the blood concentration (AUC), whereby it results to a big amount of administration and virtually increases the side effect. Therefore, in case of developing AVP as an anti-dementia drug, it is considered most ideal to make a chemical modification for increasing the BBB transition specificity, maintaining a high anti-dementia activity and changing proline of AVP 4-9 to D form to reduce the toxicity.

BBB is known as a site where fundamentally the permeability for substances is extremely slow. Especially, a substance low in the lipophlicity or a substance whose molecular weight exceeds 1000 are said to barely permeate through BBB. Therefore, a kind of peptides or proteins are classified one of substances which are hardly permeable through BBB. However, it is necessary for a nutrient into brain or an exocrine hormone to permeate through BBB, and it is recognized that they actually permeate (Pharmacol. Rev. 46:269–291; 1994). Concerning this, Pardridge (UCLA) and Terasaki, Sugiyama, et al. (Tokyo Univ.) recently found two types of transition pathways and studied a drug delivery method into the central nerve by using these (see Pharmacol. Toxicol., 71:3–10:1992 and J. Control Release, 29:163–169:1994). The first is the receptor mediated endocytosis mechanism (RME) by each kind of hormone receptor. The second is the absorptive mediated endocytosis mechanism (AME) by which a cationic substance is specifically taken in BBB. As to RME the receptor expression of insulin, transferrin, etc. in BBB is apparent. Up to date, as a drug delivery method specific to the central nerve system by utilizing RME, conjugates between a target drug and insulin or anti-transferrin antibody are actively prepared. These conjugates are shown to relatively well permeate through BBB. However, in case of administering the insulin conjugate is expected the appearance of hypoglycemia as a side effect. Further, in case of the conjugate with anti-transferrin antibody there is the problem that it is necessary to make the conjugate with a human type IgG owing to the problem of allergy.

From these, it is considered that utilizing AME is most safe and realistic as a drug delivery method specific to the central nerve system. AME is recently well noticed among researchers of drug delivery system (DDS) and is considered to do the uptake of a cationic substance into the central nerve system by the mechanism which is frequently observed in the cerebrovascular endothelial cells which constitute BBB. Especially, it is said that a substance high in the isoelectric point (PI value) permeates through BBB with a high specificity (see Zoku-Iyakuhin no Kaihatsu (Development of Drugs, second series), Vol. 4, 1991, Hirokawa).

SUMMARY OF THE INVENTION

In the above circumstances, the inventors synthesized new AVP type compounds which are estimated to have the PI value around 10, and by investigating the anti-dementia effect for these compounds by a passive avoidance test, found them to have an excellent therapeutic effect. The invention has been made on the basis of these findings.

The invention is to provide new peptides represented by the following general formula

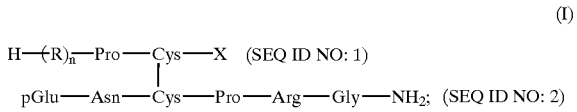

(I)

(wherein X is OH or NH$_2$, R is an amino acid residue selected from Arg, His, Lys, Methyl-Arg or Methyl-Tyr, n is an integer of 1–4, and in the case that n is 2–4, R may be identical with or different from each other) and an anti-dementia drug containing one or more of these new peptides as an active ingredient.

In the following, the invention will be explained in detail.

The new peptide compounds (denoted as C-AVP 4-9) represented by the formula (I) according to the invention are peptides consisting of 9–amino acids, wherein the N-terminal of Cys in AVP (H-(R)$_n$-Pro is removed in the above formula (I), X is a hydrogen atom; denoted as AVP 4-9) side chain is substituted with a various combination of basic amino acids such as Arg, His, Lys, Methyl-Arg or Methyl-Tyr, and they show an extremely excellent anti-dementia activity, having a high PI value and BBB permeability compared with AVP 4-9.

The peptide compounds of the invention can be synthesized by a conventional method generally used in a peptide synthesis, though, a method, in which two units cleaved at the S—S bond of Cys—Cys are each synthesized and then the S—S bonding is finally made, is convenient and preferable. In the following is illustrated C-AVP 4-9-000 (in the above formula (I), R=Arg-His) explaining its synthesis.

SYNTHETIC METHOD

1. Synthesis of unit A and unit B

The unit A (Arg-His-Pro-Cys;SEQ ID NO:3) and the unit B (pyro-Glu-Asn-Cys-Pro-Arg-Gly;SEQ ID NO:2) were synthesized according to a conventional method using Beckman 990 peptide synthesis apparatus. Namely, by using Boc-trisulfonylarginine, Boc-benzyloxymethylhistidine and 4-methylbenzylcysteine-Merrifield resin and repeating the following removal step of Boc group and the condensation step was synthesized the unit B; arginyl-histidyl-prolyl-cysteine. Further, in the same way the unit A; pyroglutamyl-asparaginyl-cysteinyl-prolyl-arginyl-glycine by using Boc-xanthylasparagine, Boc-glycine, Boc-proline, Boc-methylbenzylcysteine, pyroglutamine and 4-methylbenzhydryl-Merrifield resin.

(a) Removal Step of Boc Protective Group

To the peptide resin was added 50% trifluoroacetic acid (TFA)/dichloromethane (DCM)in the ratio of 10 ml/g, and after stirring for 5 min., the supernatant was removed. 50% TFA/DMC (5 ml/g resin) was added to the precipitate. After stirring for 25 min. the supernatant was removed, and the precipitate was washed with isopropanol, diisopropyl ethylamine and DCM two times respectively. The coupling was confirmed by Keiser test.

(b) Condensation Step 3 equivalent mol. of Boc-amino acid against the peptide resin were dissolved in 50% TFA/DCM and the solution was added to the deprotected peptide resin. Further, 3 equivalent mol. of diisopropylcarbodiimide and 1 equivalent mol. of diisopropylethylamine were added and stirred for 60–120 min. The peptide resin was washed with isopropanol and DCM two times respectively and confirmed by Keiser test. Then, by repeating the deprotection and the condensation, all the amino acids were coupled to the resin, and the resin was washed with isopropanol and DCM two times respectively and dried under reduced pressure.

2. Bonding Step of the Unit A and the Unit B (a) Final Deprotection by HF

To the peptide resin 1 g was added HF 30 ml containing 1% anisole and 1% ethanedithiol and the mixture was stirred at 0° C. for 75 min. HF was removed under reduced pressure, and the resin was let precipitate by a dry ether cooled, followed by washing with ether two times. The peptide was extracted with 5% acetic acid and freeze-dried overnight to give 300–500 mg of a crude peptide.

(b) Formation of S—S Bonding

To each equivalent mole of the A chain and the B chain was added water 2l, and the mixture was adjusted to pH 6.4 and mixed for 20 hr. By this way the aimed compound (C-AVP 4-9-000) was obtained in about 80% yield.

(c) Purification

YMC Jsphere ODS-M80 column (4.6×150 mm), eluent A; 0.05% TFA/distilled water and eluent B; acetonitrile were used, and the purification was done by HPLC at the condition that the B liquid was made 20% in 20 min.

3. Structure Confirmation by Secondary Ion Mass Spectrometry

About 200 $\mu$g of the peptide (C-AVP 4-9-000) obtained by the above synthesis were taken on a silver sample holder and mixed with glycerol 2 $\mu$l. The mass spectrum was measured by the SIMS method making Xe+(8 kV) as a first ion.

On the mass spectrum M/Z 1165 (M+H) corresponding to the molecular ion was clearly recognized, and further, each ion of M/Z 266, 363, 408, 466, 478, 512 and 544 due to the A chain and M/Z 215, 231, 259, 326, 609, 624, 656 and 688 due to the B chain were confirmed.

Furthermore, the ion (M/Z 434) in which $CO_2$ was eliminated from the M/Z 478 ion, the ion (M/Z 457) in which pGlu-Asn-NH was cleaved from the M/Z 624 ion, the ion (M/Z 746) in which glycerol was added to the B chain, and the like were found to confirm the chemical structure of C-AVP 4-9-000.

Analytical Conditions

Apparatus; HITACHI M-80B double-focus mass spectrometer

Analytical mode; glycerol SIMS

Primary ion; Xe+(8 kV)

Accelerating voltage; 3 kV

Detector; electron.multiplier (1500 V)

Scan; M/Z 0–2000/8 sec (Descan duration of 1.2 sec)

The peptide compounds synthesized according to the above synthetic method are shown in Table 1. Further, the PI value was analyzed by the isoelectrofocusing method for the peptide 5 $\mu$g using a capillary electrophoretic apparatus (Beckman P/ACE 5000) and an isoelectrofocusing kit (eCAP 3-10, Beckman). The detection was carried out by UV 214 nm.

TABLE 1

Synthesized compounds and PI values

| compounds | R | SEQ ID NO | n | X | PI values | MW |
|---|---|---|---|---|---|---|
| AVP 4-9 (control) | | | 0 | | 9.27 | 774.9 |
| C-AVP 4-9-000 | -Arg-His- | | 2 | OH | 9.77 | 1165.0 |
| C-AVP 4-9-000N | -Arg-His- | | 2 | NH$_2$ | 9.91 | 1164.5 |
| C-AVP 4-9-001 | -(Me)Arg-His- | | 2 | NH$_2$ | 9.93 | 1178.5 |
| C-AVP 4-9-002 | -(Me)Tyr-Arg- | | 2 | NH$_2$ | 9.92 | 1341.7 |
| C-AVP 4-9-003 | -(Me)Tyr-(Me)Arg-His- | | 3 | NH$_2$ | 9.83 | 1356.7 |
| C-AVP 4-9-004 | -(Me)Tyr-Arg-(Me)Arg-His- | 4 | 4 | NH$_2$ | | 1512.9 |
| C-AVP 4-9-005 | -(Me)Arg-His- | | 2 | OH | | 1179.5 |

TABLE 1-continued

Synthesized compounds and PI values

| compounds | R | SEQ ID NO | n | X | PI values | MW |
|---|---|---|---|---|---|---|
| C-AVP 4-9-006 | -(Me)Tyr-Arg-His- | | 3 | OH | | 1342.7 |
| C-AVP 4-9-007 | -(Me)Arg-Arg-His- | | 3 | OH | | 1335.7 |
| C-AVP 4-9-008 | -(Me)Tyr-Arg-Arg-His- | 5 | 4 | OH | | 1498.9 |
| C-AVP 4-9-009 | -(Me)Tyr-Arg-(Me)Arg-His- | 4 | 4 | OH | | 1512.9 |
| C-AVP 4-9-010 | -(Me)Arg-Arg-His- | | 3 | $NH_2$ | | 1334.7 |
| C-AVP 4-9-011 | -(Me)Tyr-Arg-Arg-His- | 5 | 4 | $NH_2$ | | 1635.1 |

All the peptide derivatives of the invention are extremely low in toxicity, and the appearance of toxicity was also not observed at various doses in the biological activity test concerning the anti-dementia effect.

The peptides of the invention can be administered in a free form or an appropriate salt form. As a dose is appropriate the range of 0.001–10 mg/body weight 1 kg/day on the basis of the free peptide, though, as long as the appearance of toxicity is not observed, more than this range can be administered on the situation.

There is no special restriction for the administration, though, for example, an intravenous, subcutaneous, oral, intrarectal and nasal administrations, etc., can be used.

The preparation method can be carried out in a conventional method according to each administration method. For example, they are injections, powders, tablets, suppositories, nose drops and the like.

Test for anti-dementia Effect

1. Materials and Methods

As used drugs were C-AVP 4-9-000, C-AVP 4-9-000N and C-AVP 4-9-001. Additionally, AVP 4-9 was used as a control drug.

The test solution in which each of these test drugs dissolved in saline was subcutaneously administered to rats. As to animals, male Wister rats (aged 7–9 weeks) were bought from Japan Charles River (JCR) and used after the preliminary feeding for more than one week. At the time of the preliminary feeding it lighted up from AM 8.00 to PM 8.00.

2. Passive Avoidance Test at 60 Min. Before Administration

It was carried out by partially modifying the method of Ader R. R. (Psycon. Sci., 26, p125–128, 1972). Namely, rats were let stay in a light room of the passive avoidance test apparatus consisting of a light and dark rooms, and were let move freely for 2 min. After 45 min., the rats were let stay again in the light room. When the rats went into the dark room, the electric current 0.3 mA was applied for 30 sec. by Muromachikikai SGS-002 on the floor of the dark room. Further, in all processes of the experiment the rats were let move freely between the dark room and the light room. Each peptide was subcutaneously administered at 23 hr. (1 hr. before the retention test) after the electric shock. Subsequently, the rats were let stay in the light room after 1 hr. (24 hr. after the electric shock), the time (latency) when the rats went into the dark room was measured (retention test).

FIG. 1-A, FIG. 1-B, FIG. 1-C and FIG. 1-D show the test results of AVP 4-9, C-AVP 4-9-000, C-AVP 4-9-000N and C-AVP 4-9-001 respectively.

In these results, the doses of C-AVP 4-9-000 and C-AVP 4-9-000N at the maximum effect are $\frac{1}{100}$ compared with that of AVP 4-9, indicating that their effect is much increased.

3. Passive Avoidance Test at 180 Min. Before Administration

The test was carried out according to the test 2 except that the administration of the test solution was made at 21 hr. (3 hr. before the retention test) after the electric shock. FIG. 2-A, FIG. 2-B, FIG. 2-C and FIG. 2-D show the test results of AVP 4-9, C-AVP 4-9-000, C-AVP 4-9-000N and C-AVP 4-9-001 respectively.

In these results, AVP 4-9 did not show any significant effectiveness at each dose which was administered 3 hours in advance of the test. On the contrary, it was found that C-AVP 4-9-000N and C-AVP 4-9-0001 showed the significant effectiveness even though the administration was 3 hr. before the test.

4. Trend in Blood Concentration of C-AVP 4-9-000

C-AVP 4-9-000 (389 Ci/mmol) labeled with $^{125}I$ by the chloramine-T method was administered (i.v.) to mice in 1 $\mu$Ci, $^{125}$I-C-AVP 4-9-000 in plasma was quantitated by separating the methanol extract using Radio-HPLC. The results are shown in FIG. 3.

5. Evaluation of Brain Transition of C-AVP 4-9-000

In the same way, the anti-staphylokinase antibody (16 Ci/mmol, AS22; There is no antigen in mouse body. It is used as a marker which does not transit into brain and remains in blood vessel.) labeled with chloramine-T and $^{125}$I-C-AVP 4-9-000 prepared in 4 were administered at 1 $\mu$ci/mouse (JCR, male ICR strain) respectively, and cerebrum, cerebellum and spinal cord were taken out at the time (6 hr. in AS22, 15 min. in C-AVP 4-9-000) of the apparent equilibrium in the plasma concentration. In the case of AS22, the radioactivity contained in the trifluoroacetic acid precipitate fraction was made the $^{125}$I-AS22 amount. Further, $^{125}$I-C-AVP 4-9-000 was quantitated by separating the methanol extract using Radio-HPLC. The results are shown in Table 2.

In these results, AS22 scarcely transited into brain. On the contrary, it is understood that C-AVP 4-9-000 transited into brain in a sufficient concentration.

TABLE 2

$^{125}$I-C-AVP 4-9-000 distribution in CNS after i.v. administration

| $^{125}$I-C-AVP 4-9-000 (conc.) | | Kp value (ml/g tissue) | |
|---|---|---|---|
| tissue | (fmol/g tissue) | $^{125}$I-C-AVP | $^{125}$I-AS22 |
| cerebellum | 12.6 ± 3.7 | $1.4 \times 10^{-1} \pm 4.5 \times 10^{-3}$ | $8.4 \times 10^{-3} \pm 2.8 \times 10^{-3}$ |
| cerebrum | 15.6 ± 1.1 | $1.8 \times 10^{-1} \pm 4.5 \times 10^{-2}$ | $7.6 \times 10^{-3} \pm 5.2 \times 10^{-3}$ |
| spinal cord | 15.8 ± 7.3 | $1.7 \times 10^{-1} \pm 5.2 \times 10^{-2}$ | $1.4 \times 10^{-2} \pm 1.3 \times 10^{-3}$ |

6. Intracerebral Metabolism of C-AVP 4-9-000

C-AVP 4-9 series compound can be hydrolyzed in brain by the action of prolyl endopeptidase, and it is considered that they are converted to AVP 4-9.

Therefore, 500 μM of C-AVP 4-9-000 were incubated (6 hr., 37° C.) with a rat cerebral homogenate (100 μg/rat) in the presence or in the absence of carbobenzoyloxy prolyl-prolinal (ZPP, 20 μM) as known as a potent inhibitor for propyl endopeptitase. After incubation metabolites were extracted with methanol. The metabolites were analyzed by HPLC. Further, ZPP is a specific inhibitor for prolyl endopeptidase. After methanol extraction, the metabolites were quantitated by the separation with HPLC. The results are shown in Table 3.

In these results, under the presence of ZPP, C-AVP 4-9 remained in a considerable amount even after 6 hour's incubation, and the formation of AVP 4-9 was almost not observed. On the contrary, under the absence of ZPP (actual model), C-AVP 4-9 scarcely remained after 6 hour's incubation, and on one hand, the formation of AVP 4-9 was observed. It is considered that the compound of the invention acts after it is changed in brain to the active form by the action of prolyl endopeptidase.

TABLE 3

Conversion of C-AVP 4-9-000 to AVP 4-9 by brain homogenate

| incubate | peak area (% vs control) | | |
| --- | --- | --- | --- |
| Time ZPP (h) | C-AVP 4-9-000 (15.02 min) | AVP 4-9 (12.05 min) | Unknown (14.02 min) |
| 0 | −100.00 ± 5.79 | 1.85 ± 0.13 | 0.48 ± 0.00 |
|   | +114.35 ± 15.79 | 2.86 ± 4.40 | 0.54 ± 0.10 |
| 6 | −0.05 ± 0.02 | 25.14 ± 0.34 | 18.43 ± 0.13 |
|   | +49.10 ± 0.40 | 3.79 ± 0.09 | 17.60 ± 0.14 |

Figure 1A:
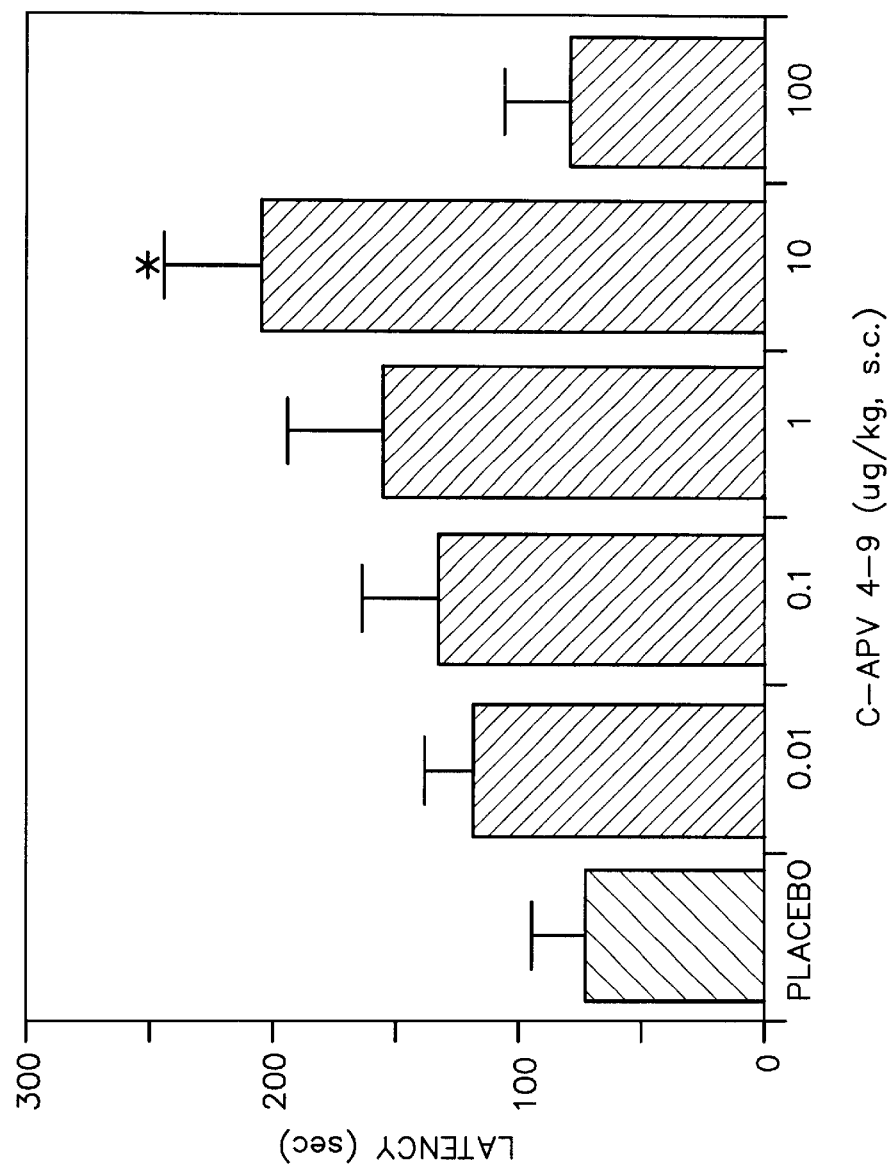
FIG. 1-A
Figure 1B:
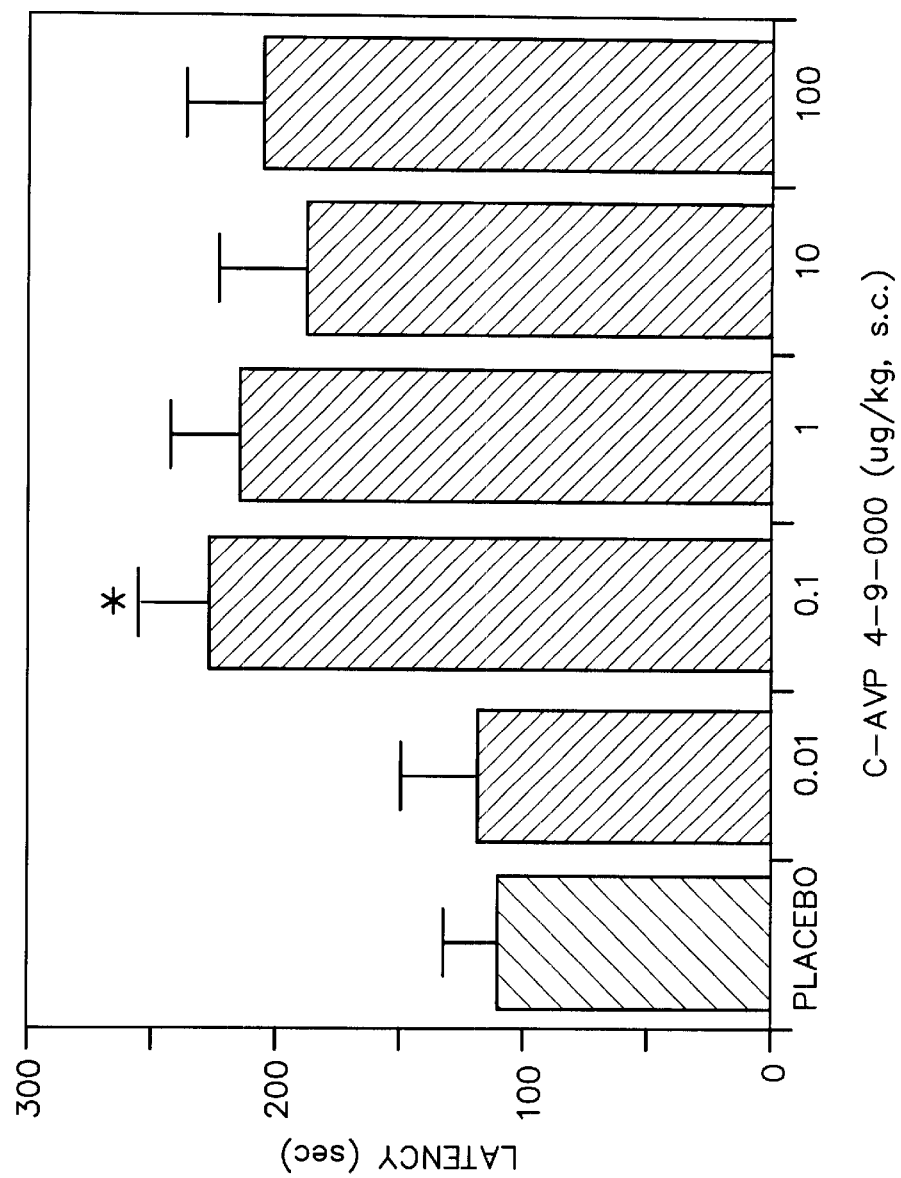
Figure 1C:
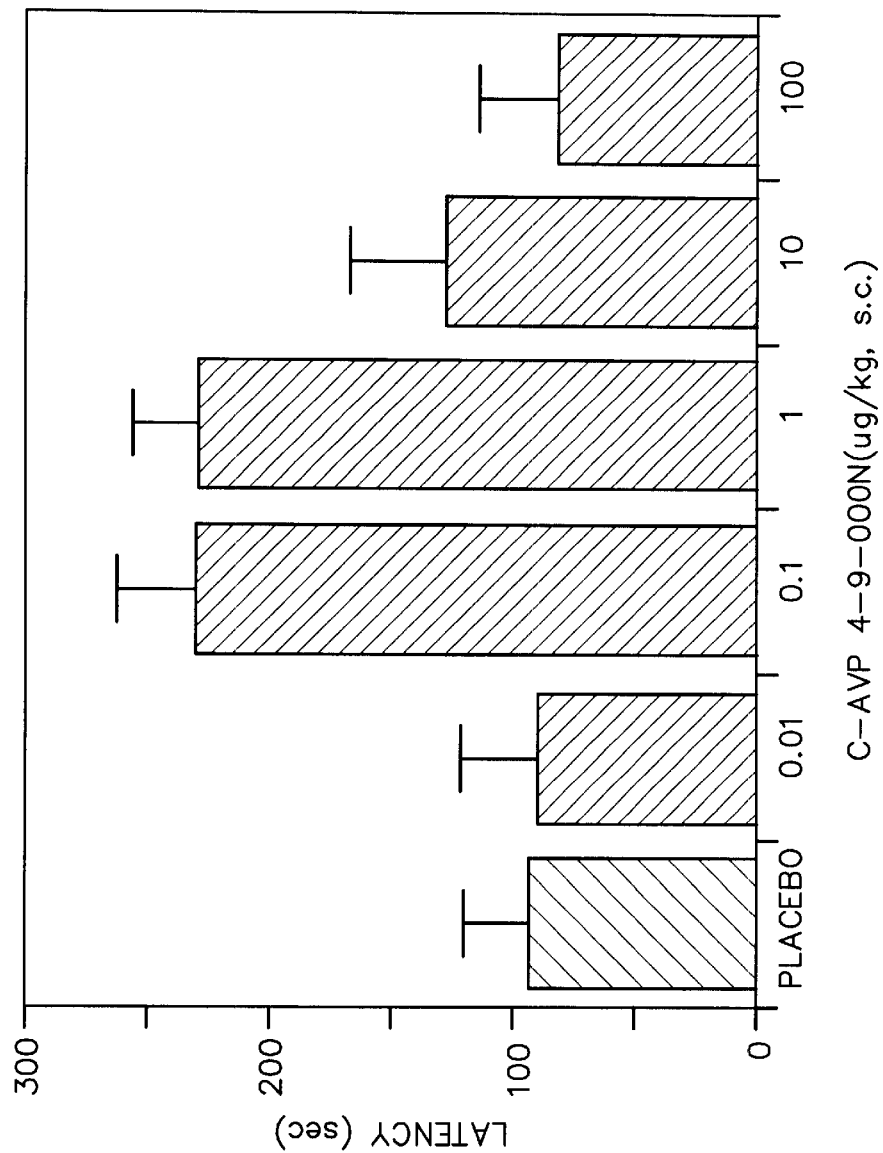
Figure 1D:
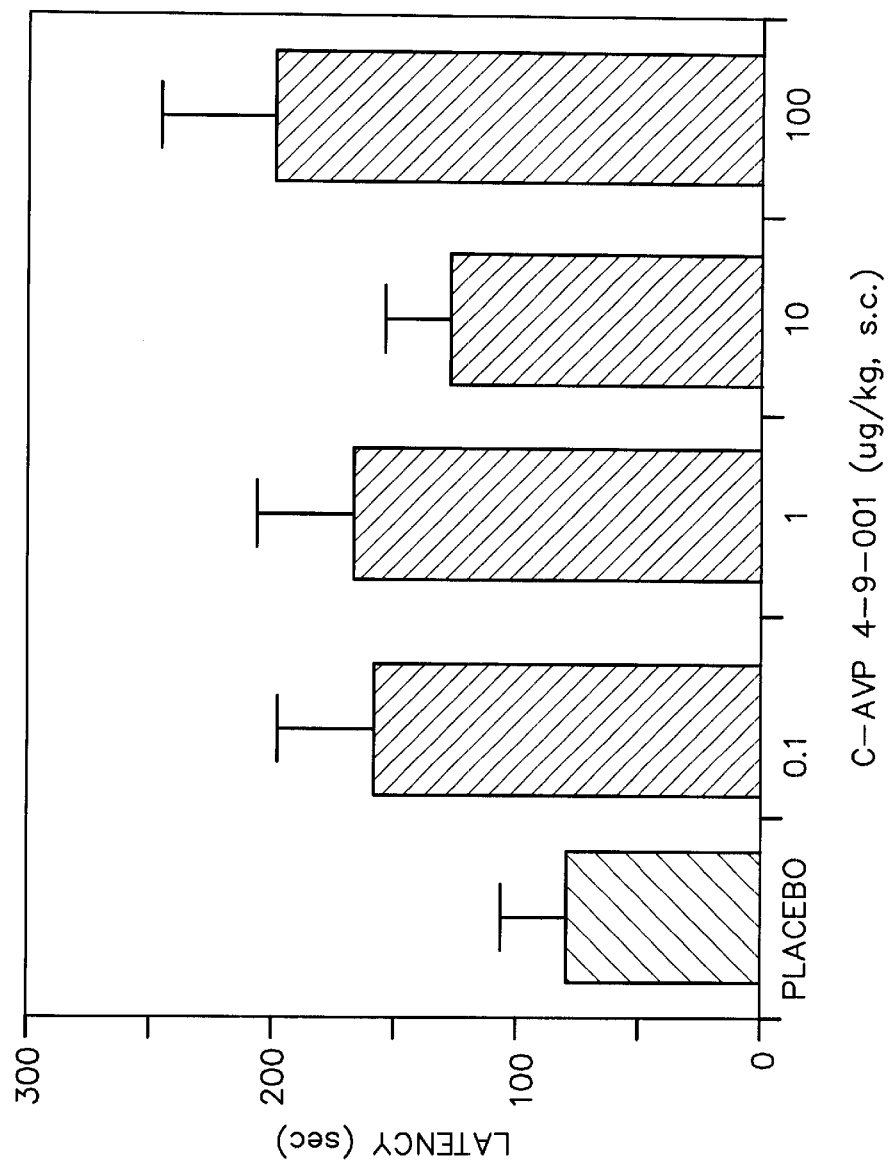
Figure 2A:
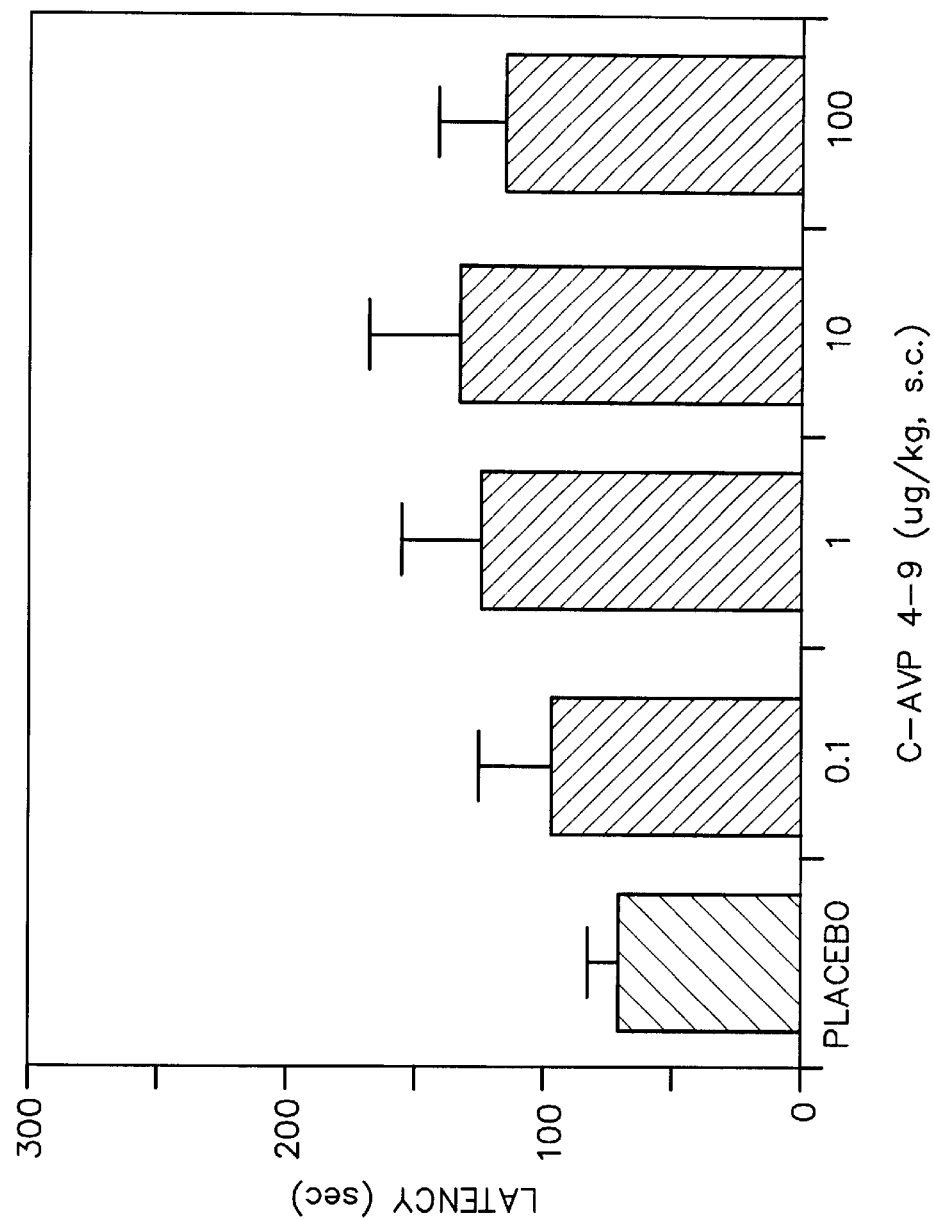
Figure 2C:
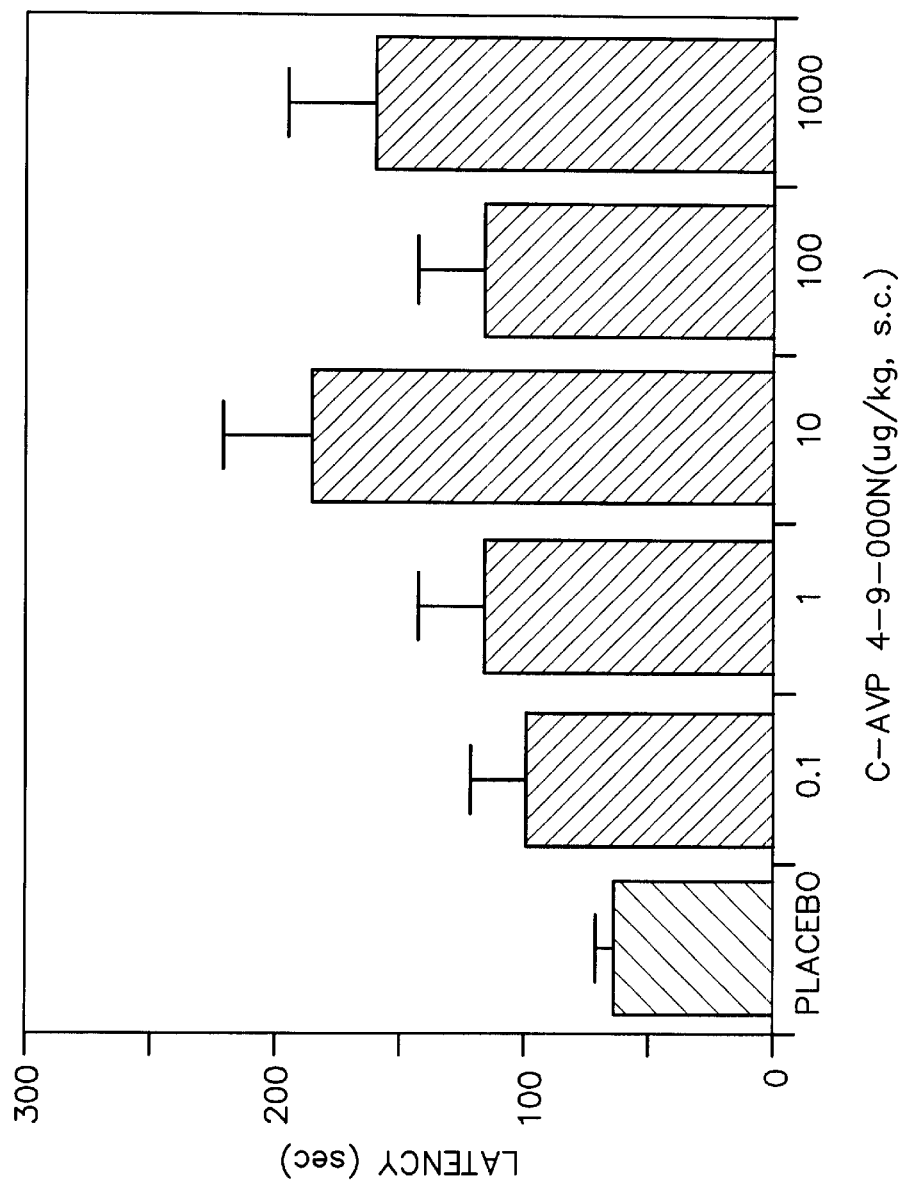
Figure 2D:
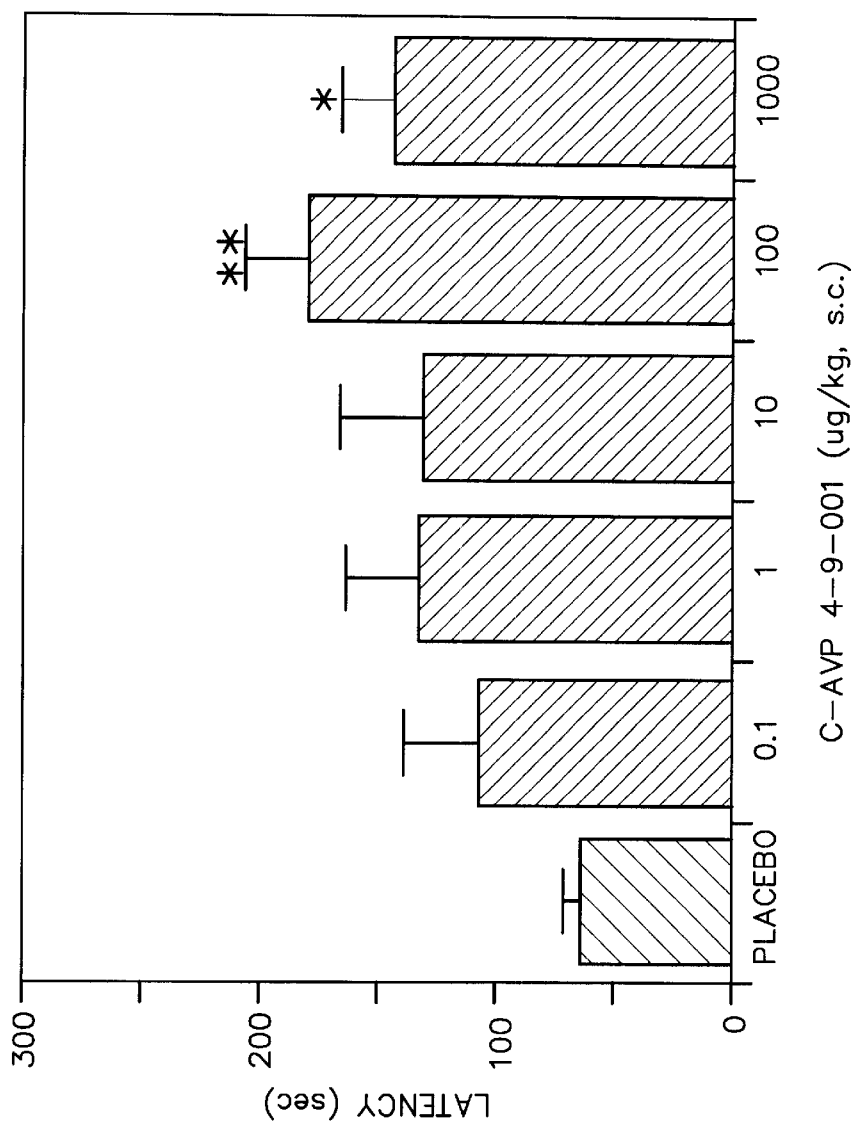
Figure 3:
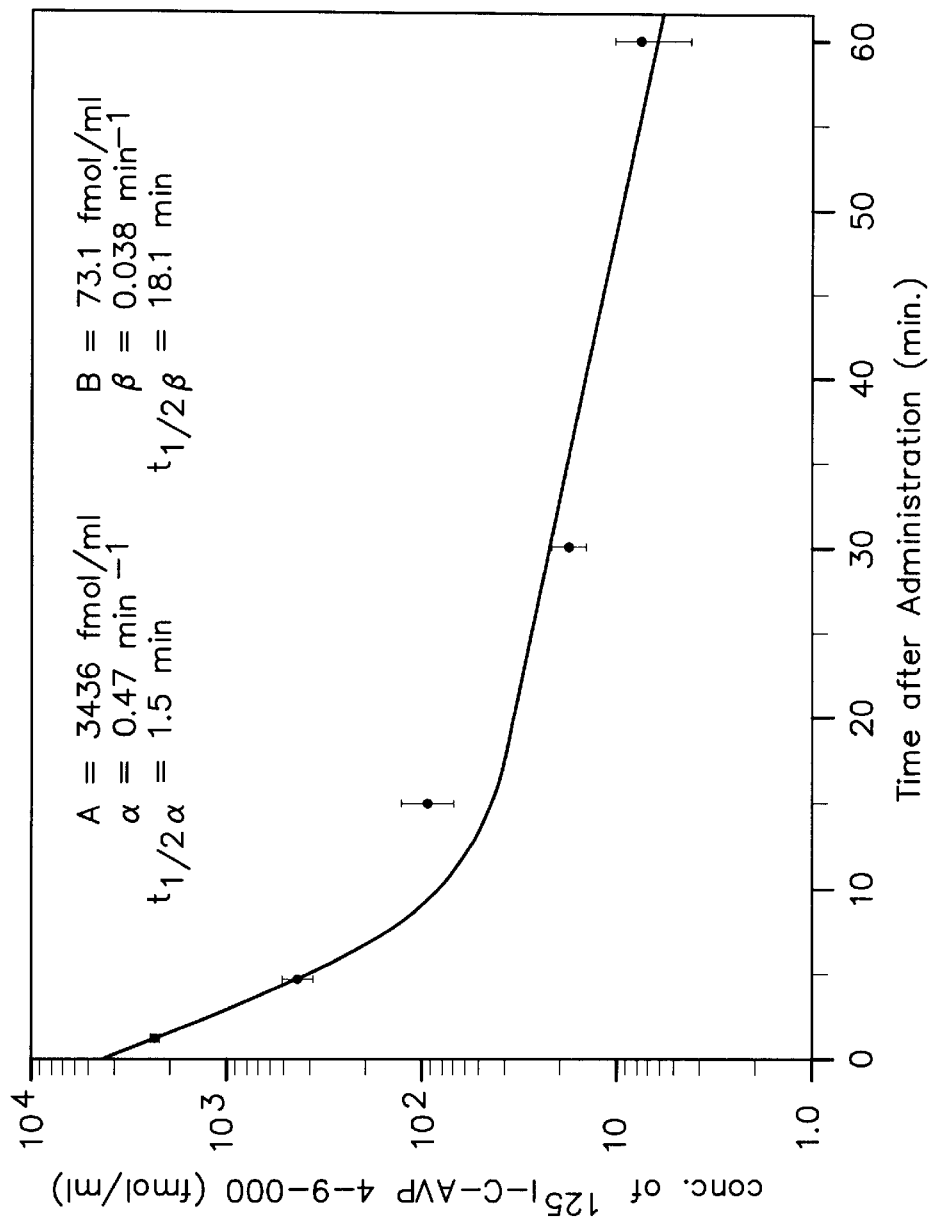

It is the figure which shows the effect on the rat passive avoidance for AVP 4-9 administered at 60 min. before the retention test. The latency is shown in the case of the s.c. administration of the described amount of AVP 4-9 at 60 min. before the retention test. Each bar means mean value±S.E.M (n is not less than 8). (* $p<0.05$, Kruskal-Wallis test and subsequent Dunnet't test)

FIG. 1-B

It is the figure which shows the effect on the rat passive avoidance for C-AVP 4-9-000 administered at 60 min. before the retention test. The latency is shown in the case of the s.c. administration of the described amount of C-AVP 4-9-000 at 60 min. before the retention test. Each bar means mean value±S.E.M (n is not less than 10). (* $p<0.05$, Kruskal-Wallis test and subsequent Dunnet't test)

FIG. 1-C

It is the figure which shows the effect on the rat passive avoidance for C-AVP 4-9-000N administered at 60 min. before the retention test. The latency is shown in the case of the s.c. administration of the described amount of C-AVP 4-9-000N at 60 min. before the retention test. Each bar means mean value±S.E.M (n is not less than 8).

FIG. 1-D

It is the figure which shows the effect on the rat passive avoidance for C-AVP 4-9-001 administered at 60 min. before the retention test. The latency is shown in the case of the s.c. administration of the described amount of C-AVP 4-9-001 at 60 min. before the retention test. Each bar means mean value±S.E.M (n is not less than 8).

FIG. 2-A

It is the figure which shows the effect on the rat passive avoidance for AVP 4-9 administered at 180 min. before the retention test. The latency is shown in the case of the s.c. administration of the described amount of AVP 4-9 at 180 min. before the retention test. Each bar means mean value±S.E.M (n is not less than 11).

FIG. 2-B

It is the figure which shows the effect on the rat passive avoidance for C-AVP 4-9-000 administered at 180 min. before the retention test. The latency is shown in the case of the s.c. administration of the described amount of C-AVP 4-9-000 at 180 min. before the retention test. Each bar means mean value±S.E.M (n is not less than 11). (* $p<0.05$, Kruskal-Wallis test and subsequent Dunnet't test)

FIG. 2-C

It is the figure which shows the effect on the rat passive avoidance for C-AVP 4-9-000N administered at 180 min. before the retention test. The latency is shown in the case of the s.c. administration of the described amount of C-AVP 4-9-000N at 180 min. before the retention test. Each bar means mean value±S.E.M (n is not less than 11).

FIG. 2-D

It is the figure which shows the effect on the rat passive avoidance for C-AVP 4-9-001 administered at 180 min. before the retention test. The latency is shown in the case of the s.c. administration of the described amount of C-AVP 4-9-001 at 180 min. before the retention test. Each bar means mean value±S.E.M (n is not less than 11). (* $p<0.05$, Kruskal-Wallis test and subsequent Dunnet't test)

FIG. 3

It is the figure which shows a transient change of the plasma concentration of C-AVP 4-9-000.

What is claimed is:

1. An isolated peptide represented by the following general formula

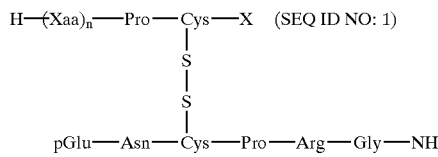  (I)

wherein X is OH or NH$_2$, Xaa is an amino acid residue selected from the group consisting of Arg, His, Lys, N-methyl-Arg and N-methyl-Tyr, n is an integer of 1 to 4, and in the case that n is 2 to 4, each Xaa may be identical with or different from each other Xaa.

2. The peptide of claim 1, wherein X is OH.
3. The peptide of claim 1, wherein X is NH$_2$.
4. The peptide of claim 1, wherein Xaa is Arg.
5. The peptide of claim 1, wherein Xaa is His.
6. The peptide of claim 1, wherein n is 2.
7. A composition containing one or more peptides represented by the following general formula

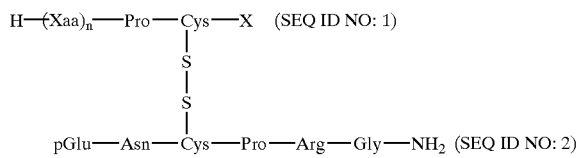  (I)

wherein X is OH or NH$_2$, Xaa is an amino acid residue selected from the group consisting of Arg, His, Lys, N-methyl-Arg and N-methyl-Tyr, n is an integer of 1 to 4, and in the case that n is 2 to 4, each Xaa may be identical with or different from each other Xaa.

8. The composition of claim 7, further comprising an acceptable carrier.
9. The composition of claim 7, wherein X is OH.
10. The composition of claim 7, wherein X is NH$_2$.
11. The composition of claim 7, wherein Xaa is Arg.
12. The composition of claim 7, wherein Xaa is His.
13. The composition of claim 7, wherein n is 2.
14. An anti-dementia composition containing one or more peptides represented by the following general formula

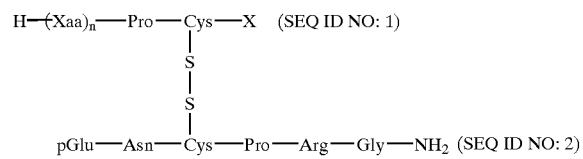  (I)

wherein X is OH or NH$_2$, Xaa is an amino acid residue selected from the group consisting of Arg, His, Lys, N-methyl-Arg and N-methyl-Tyr, n is an integer of 1 to 4, and in the case that n is 2 to 4, each Xaa may be identical with or different from each other Xaa.

15. The anti-dementia composition of claim 14, further comprising a pharmaceutically acceptable carrier.
16. The anti-dementia composition of claim 14, wherein X is OH.
17. The anti-dementia composition of claim 14, wherein X is NH$_2$.
18. The anti-dementia composition of claim 14, wherein Xaa is Arg.
19. The anti-dementia composition of claim 14, wherein Xaa is His.
20. The anti-dementia composition of claim 14, wherein n is 2.

* * * * *